US009670465B2

(12) United States Patent
Atarashi et al.

(10) Patent No.: US 9,670,465 B2
(45) Date of Patent: Jun. 6, 2017

(54) NON-ENTOMOPHILOUS TOMATO YELLOW LEAF CURL VIRUS

(75) Inventors: Hiroki Atarashi, Noda (JP); Toshiro Inoue, Noda (JP); Haruki Sayama, Noda (JP); Hisashi Nishigawa, Utsunomiya (JP); Tamotsu Murai, Utsunomiya (JP); Tomohide Natsuaki, Utsunomiya (JP)

(73) Assignee: KIKKOMAN CORPORATION, Chiba (JP)

( * ) Notice: Subject to any disclaimer, the term of this patent is extended or adjusted under 35 U.S.C. 154(b) by 627 days.

(21) Appl. No.: 13/983,442

(22) PCT Filed: Feb. 3, 2012

(86) PCT No.: PCT/JP2012/052530

§ 371 (c)(1),
(2), (4) Date: Dec. 12, 2013

(87) PCT Pub. No.: WO2012/105696

PCT Pub. Date: Aug. 9, 2012

(65) Prior Publication Data

US 2014/0227230 A1 Aug. 14, 2014

(30) Foreign Application Priority Data

Feb. 4, 2011 (JP) ................................ 2011-023199

(51) Int. Cl.

| | |
|---|---|
| ***C12N 15/82*** | (2006.01) |
| ***C12N 7/00*** | (2006.01) |
| ***C12Q 1/70*** | (2006.01) |
| ***A61K 39/12*** | (2006.01) |
| ***C07K 14/005*** | (2006.01) |

(52) U.S. Cl.

CPC ................ *C12N 7/00* (2013.01); *A61K 39/12* (2013.01); *C07K 14/005* (2013.01); *C12Q 1/70* (2013.01); *C12N 2750/12021* (2013.01); *C12N 2750/12022* (2013.01); *C12N 2750/12034* (2013.01)

(58) Field of Classification Search

None

See application file for complete search history.

(56) References Cited

U.S. PATENT DOCUMENTS

| | | | | |
|---|---|---|---|---|
| 2010/0071088 A1* | 3/2010 | Sela | .................. | C12N 15/8282 800/279 |
| 2010/0212048 A1 | 8/2010 | Hoogstraten et al. | | |

FOREIGN PATENT DOCUMENTS

| | | |
|---|---|---|
| JP | 08103163 | 4/1996 |
| JP | 11313544 | 11/1999 |
| JP | 2003304743 | 10/2003 |
| JP | 2005040067 | 2/2005 |
| JP | 2005237380 | 9/2005 |

OTHER PUBLICATIONS

Ueda et al, J Gen Plant Pathol (2004) 70:232-238.*

Lefeuvre et al, PLoS Pathog (2010) 6(10): el001164.*

Onuki et al, GenBank Accession No. AB110217.*

Hoff et al (2009) BMC Genomics 10:1-9.*

Fauquet et al., "Revision of taxonomic criteria for species demaracation in the family Geminiviridae, and an updated list of begomorvious species," Arch Virol (2003) 148:405-421.

00.029.Geminiviridae—ICTVdB Index of Viruses, http://ictvdb.bio-mirror.cn/Ictv/fs_gemin.htm, printed on May 27, 2015, 18 pages.

Fauquet et al.,"Virus Taxonomy," Eighth Report of the International Committee on Taxonomy of Viruses, 2005, Elsevier, Inc., cover, copyright, and 321-322 pages.

Noris et al., "Amino Acids in the Capsid Protein of Tomato Yellow Leaf Curl Virus That Are Crucial for Systemic Infection, PArticle Formation, and Insect Transmission," Journal of Virology, vol. 72, No. 12, Dec. 1988, pp. 10050-10057, XP002730988.

Honda, Ken-ichiro, "Recent Progress on Tomato Yellow Leaf Curl and its Vector Whitefly Researches" Proceedings of Vegetable and Tea Science, 2006, No. 3 (Final Issue), pp. 115-122.

Ji, Yuanfu, "Sources of Resistance, Inheritance, and Location of Genetic Loci Conferring Resistance to Members of the Tomato-Infecting Begomoviruses", H. Czosnek (ed.), Tomato Yellow Leaf Curl Virus Disease, 343-362, 2007 Springer.

Saito, Atsushi, "The Present Situations and Problems of Tomato Breeding Resistant to Yellow Leaf Curl", National Agriculture and Bio-oriented Research Organization, National Institute of Vegetable and Tea Science No. 3, pp. 99-102, 2006.

Saito, A., et al. "Evaluation of commerical cultivars resistant to Tomato yellow leaf curl virus using quantitative real-time PCR in tomato (Solanum lycopersicum)", National Agriculture and Food Research Organization, National Institute of Vegetable and Tea Science, Hort. Res. (Japan) No. 7, Suppl. 1, p. 107, 2008.

LeFauvre, Pierre, et al., "The Spread of Tomato Yellow Leaf Curl virus from the Middle East to the World", Plos Pathogens, 2010, 10, vol. 6, Issue 10, e1001164.

Hallan, V., et al. "Tomato yellow leaf curl virus (TYLCV) capsid protein (CP) subunit interactions: implications for viral assembly", Arch, Virol., 2001, vol. 46, p. 1765-1773.

Cohen, S., et al., "Periodic, Rather Than Continual Acquisition of a New Tomato Virus by Its Vector, the Tobacco Whitefly (Bemisia Tabaci Gennadius)", The volcani Institute of Agricultural Research, Beit Dagan, Israel, and The Hebrew University, Faculty of Agriculture, Rehovot, Israel, Ent. exp. & appl. 7 (1964); 155-166. North-Holland Publishing Co., Amsterdam.

Kato, Kimihiko, et al., The First Occurrence of Tomato Yellow Leaf Curl Virus in Tomato (Lycopersicon esulentum Mill.) in Japan, Ann. Phytopathol. Soc. Japan, 1998, vol. 64, p. 552-559.

Onuki, M., et al. "Nucleotide Sequence of a Geminivirus Occurred on Tomato in Nagasaki Prefecture" Japanese Journal of Phytopathology, 1997, vol. 63, No. 6, p. 482.

(Continued)

*Primary Examiner* — Elizabeth McElwain

(74) *Attorney, Agent, or Firm* — Buchanan Ingersoll & Rooney PC

(57) ABSTRACT

An object of the present invention is to provide a novel method of controlling TYLCV whereby the infection cycle of TYLCV can be broken. The present invention provides a novel virus that is not transmitted by an insect vector as a tomato yellow leaf curl virus. The present invention also provides a method of controlling a tomato yellow leaf curl disease and a method of preventing transmission of a yellow leaf curl virus by using a tomato yellow leaf curl virus not transmitted by an insect vector.

11 Claims, 4 Drawing Sheets

(56) References Cited

OTHER PUBLICATIONS

Kitamura, Toshio et al., "Tomato Yellow Leaf Curl Virus", Annual Report of the Kansai Plant Protection Society, 2009, vol. 51, pp. 81-83.

Zamir, D., Mapping and introgression of a tomato yellow leaf curl virus tolerance gene, TY-1, Theor. Appl. Genet., 1994, vol. 88, p. 141-146.

Hanson, Peter M., et al., "Mapping a Wild Tomato Introgression Associated with Tomato Yellow Leaf Curl Virus Resistance in a Cultivated Tomato Line", J. Amer. Soc. Hort. Sci. 125(1): 15-20, 2000.

Powell Abel, Patricia, et al., "Delay of Disease Development in Transgenic Plants that Express the Tobacco Mosaic Virus Coat Protein Gene", Science vol. 232, pp. 738-743, 1986.

Gonsalves, Dennis, "Control of Papaya Ringsport virus in Papaya: A Case Study" Ann. Rev. Phytopathol, 1998, vol. 70, pp. 415-437.

"Vegetable Horticulture Dictionary" edited by Shimizu, S. (Yasi-Engel-Daijten), Yokendo, 1977, p. 289.

Fauquet, C.M., et al., "Virus Taxonomy" Eighth Report of the International Committee on Taxonomy of Viruses, Virology Division International Union of Microbiological Societies, 2005, Elsevier, Inc., cover and copyright page.

Ji, Yuanfu, et al. "Ty-3, begomovirus resistance locus linked to Ty-1 on chromosome 6 of tomato" University of Florida, IFAS, Gulf Coast Research & Eduction Center, pp. 22-24.

* cited by examiner

FIG. 2

| | isolates | MP 116aa | CP 258aa | | | | | REn 134aa | | TrAP 135aa | C4 97aa | |
|---|---|---|---|---|---|---|---|---|---|---|---|---|
| | position | 20 | 80 | 147 | 171 | 195 | 234 | 38 | 40 | none | 23 | 29 |
| Seq. No. 20 | 17G | V | R | F | N | M | A | P | Q | match | S | H |
| Seq. No. 21 | 10-1 | L | Q | Y | K | I | S | P | L | match | S | Q |
| Seq. No. 22 | mix8-2 | L | Q | Y | K | I | S | P | L | match | S | Q |
| Seq. No. 23 | Nagasaki | L | Q | Y | K | M | A | P | L | match | S | Q |
| Seq. No. 24 | Omura (Eustoma) | L | Q | Y | K | M | A | P | L | match | S | Q |
| Seq. No. 25 | Miyazaki | L | Q | Y | K | M | A | R | L | match | P | Q |
| | Positives | + | + | + | | + | + | | | | | |

FIG. 3

| | isolates \ gene / position | Rep 357aa 6 | 18 | 52 | 73 | 80 | 164 | 168 | 213 | 217 | 340 |
|---|---|---|---|---|---|---|---|---|---|---|---|
| Seq. No. 26 | 17G | <u>K</u> | N | G | F | <u>H</u> | <u>N</u> | D | <u>M</u> | <u>V</u> | <u>S</u> |
| Seq. No. 27 | 10-1 | N | <u>K</u> | G | F | N | S | D | I | I | A |
| Seq. No. 28 | mix8-2 | N | <u>K</u> | <u>E</u> | F | N | S | D | I | I | A |
| Seq. No. 29 | Nagasaki | N | N | G | F | N | S | <u>G</u> | I | I | A |
| Seq. No. 30 | Omura (Eustoma) | N | N | G | F | N | S | D | I | I | A |
| Seq. No. 31 | Miyazaki | N | N | G | <u>S</u> | N | S | D | I | I | A |
| | Positives | | | | | + | + | | + | + | + |

```
SEQ ID NO.7_17G                   MSKRPGDIIISTPVSKVRRRLNFDSPYSSRAAVPIVQGTNKRRSWTYRPMYRKPRIYRMY
SEQ ID NO.8_ISR10-1-17Gchimera    MSKRPGDIIISTPVSKVRRRLNFDSPYSSRAAVPIVQGTNKRRSWTYRPMYRKPRIYRMY
SEQ ID NO.9_ISR10-1               MSKRPGDIIISTPVSKVRRRLNFDSPYSSRAAVPIVQGTNKRRSWTYRPMYRKPRIYRMY
                                  ************************************************************

SEQ ID NO.7_17G                   RSPDVPRGCEGPCKVQSYERRDDIKHTGIVRCVSDVTRGSGITHRVGKRFCVKSIYFLGK
SEQ ID NO.8_ISR10-1-17Gchimera    RSPDVPRGCEGPCKVQSYERRDDIKHTGIVRCVSDVTRGSGITHRVGKRFCVKSIYFLGK
SEQ ID NO.9_ISR10-1               RSPDVPRGCEGPCKVQSYEQRDDIKHTGIVRCVSDVTRGSGITHRVGKRFCVKSIYFLGK
                                  *******************:****************************************

SEQ ID NO.7_17G                   VWMDENIKKQNHTNQVMFFLVRDRRPFGSSPMDFGQVFNMFDNEPSTATVNNDLRDRFQV
SEQ ID NO.8_ISR10-1-17Gchimera    VWMDENIKKQNHTNQVMFFLVRDRRPFGSSPMDFGQVFNMFDNEPSTATVNNDLRDRFQV
SEQ ID NO.9_ISR10-1               VWMDENIKKQNHTNQVMFFLVRDRRPYGSSPMDFGQVFNMFDNEPSTATVKNDLRDRFQV
                                  **************************:***********************:*********

SEQ ID NO.7_17G                   MRKFHATVIGGPSGMKEQALVKRFFKINSHVTYNHQEAAKYENHTENALLLYMACTHASN
SEQ ID NO.8_ISR10-1-17Gchimera    MRKFHATVIGGPSGIKEQALVKRFFKINSHVTYNHQEAAKYENHTENALLLYMSCTHASN
SEQ ID NO.9_ISR10-1               MRKFHATVIGGPSGIKEQALVKRFFKINSHVTYNHQEAAKYENHTENALLLYMSCTHASN
                                  **************:**************************************:******

SEQ ID NO.7_17G                   PVYATMKIRIYFYDSISN
SEQ ID NO.8_ISR10-1-17Gchimera    PVYATMKIRIYFYDSISN
SEQ ID NO.9_ISR10-1               PVYATMKIRIYFYDSISN
                                  ******************
```

FIG. 4

NON-ENTOMOPHILOUS TOMATO YELLOW LEAF CURL VIRUS

The instant application contains a Sequence Listing which has been submitted in ASCII text file format via EFS-Web and is hereby incorporated by reference in its entirety. Said ASCII copy, created on Dec. 5, 2013, and submitted via EFS-Web on Dec. 12, 2013, is named PCT_Sequence_Listing.txt and is 23,017 bytes in size.

TECHNICAL FIELD

The present invention relates to a non insect-mediated tomato yellow leaf curl virus.

BACKGROUND ART

The tomato yellow leaf curl virus (hereinafter occasionally referred to as "TYLCV") is a type of relatively novel plant virus that was discovered in Israel in 1964.

In Japan, cases of tomato yellow leaf curl disease caused by TYLCV were discovered concurrently in 1996 in Nagasaki Prefecture, Aichi Prefecture and Shizuoka Prefecture. Tomato yellow leaf curl disease then spread rapidly in areas of greenhouse tomato production. Particularly extensive outbreaks have occurred since 2000 in Kyushu region, which is a main production area of fresh market tomato, and on many farms all of the cultivated tomatoes have been damaged by TYLCV. In each prefecture, farmers have been warned to take special care, and intense efforts have been made to prevent TYLCV by pesticide application and the like, but TYLCV damage still continues.

Symptoms of tomato yellow leaf curl disease begin with yellowing of tomato leaves, which subsequently become deformed as the leaf edges gradually curl under. When symptoms are severe, leaves of an entire tomato plant appear like permed hair. Symptoms do not extend to fruit, but if tomato is infected with TYLCV at an early stage of growth, only up to about the second bunch of fruit will be set, causing serious losses amounting to a 70% to 80% reduction in yield.

Tomato yellow leaf curl disease becomes persistent and pervasive when it is transmitted by the whitefly *Bemisia tabaci* (Gennadius), which is an insect vector of TYLCV.

Meanwhile, there are no effective antiviral agents against plant viruses. Up until now, the most common methods of controlling plant viruses have been by applying pesticides to kill insect vectors that transmit viruses, using insect-proof nets and repellent materials to physically prevent entry of insect vectors to cultivation facilities, and sterilizing soil, removing infected plants, sterilizing cultivation tools, using barrier crops, and planting virus-tolerant crops.

The same applies to control of TYLCV, and main methods used for disrupting infection cycle of TYLCV involve controlling *Bemisia tabaci* which is an insect vector of TYLCV and removing infected plants at an early stage (Non-patent Document 1).

However, if insect-proof nets with a mesh of 0.4 mm or less effective for prevention of entry in order to control *Bemisia tabaci* are used, it is concerned about temperature elevation in cultivation facilities and thus *Bemisia tabaci* control using insect-proof nets is difficult to implement in the field.

Moreover, a variety of tomato cultivars with different growing seasons are grown in Kyushu region which is a major tomato producing area, so that tomatoes are being grown somewhere at every time of year. As a result, *Bemisia*

*tabaci* carrying TYLCV is not killed off by winter cold because *Bemisia tabaci* moves between outdoor farms and indoor facilities according to a variety of tomato cultivars, making TYLCV control difficult because there is no interruption in infection cycle of TYLCV.

Moreover, an insecticide-tolerant *Bemisia tabaci* referred to *Bemisia tabaci* biotype Q (hereinafter occasionally referred to as "*Bemisia tabaci* Q") has recently begun to proliferate, restricting usefulness of pesticide control.

Looking at TYLCV tolerant tomatoes, genes such as Ty-1, Ty-2, Ty-3 have been discovered in wild tomatoes. When tomatoes have these genes, virus concentrations are reduced within the tomatoes and symptoms are suppressed, but TYLCV infection itself is not arrested (Non-patent Documents 2 and 3).

Tomatoes having these genes introduced by hybridization have already appeared on the market, but due to the nature of these genes, it is known that in all cases the tomatoes are liable to infection by TYLCV and then viruses proliferate inside the tomatoes (Non-patent Document 4).

Therefore, if *Bemisia tabaci* control is neglected when tomatoes with these introduced genes are cultivated, the tomatoes will carry TYLCV even if symptoms by TYLCV are suppressed, and will become sources of TYLCV infection, placing any susceptible tomato varieties in the surrounding area at serious risk of TYLCV infection.

CITATION LIST

Non-Patent Literature

Non-Patent Literature 1: Honda, Proceedings of Vegetable and Tea Science No. 3, pp. 115-122, 2006

Non-Patent Literature 2: Henryk Czosnek, Tomato Yellow Leaf Curl Virus Disease, Springer, pp. 343-362, 2007

Non-Patent Literature 3: Saito, Proceedings of Vegetable and Tea Science No. 3, pp. 99-102, 2006

Non-Patent Literature 4: Saito et al., Hort. Res. (Japan) No. 7, Suppl. 1, p. 107, 2008

SUMMARY OF INVENTION

Technical Problem

Thus, the spread of TYLCV cannot be adequately controlled with conventional plant virus control methods such as those discussed above, and there are many problems with each of these control methods. Moreover, since none of the conventional control methods disrupts the TYLCV infection cycle, there is a need for a novel TYLCV control method capable of disrupting the TYLCV infection cycle.

Solution to Problem

As a result of exhaustive research aimed at solving these problems, the inventors found a solution to these problems by discovering a novel virus that is not transmitted by an insect vector, thereby perfecting the present invention.

The present invention relates to the following:

[1] A tomato yellow leaf curl virus not transmitted by an insect vector.

[2] The virus according to [1], wherein the insect vector is whitefly *Bemisia tabaci* (Gennadius).

[3] The virus according to [1] or [2], having DNA represented by the nucleotide sequence of SEQ ID NO:1, SEQ ID NO:2, SEQ ID NO:4 or SEQ ID NO:5.

[4] The virus according to any one of [1] to [3], having the following peptide:

(1) a peptide represented by the amino acid sequence of SEQ ID NO:7 or SEQ ID NO:8;

(2) a peptide represented by the amino acid sequence of SEQ ID NO:7 or SEQ ID NO:8 with one or more amino acids deleted, added, and/or substituted therein.

[5] The virus according to any one of [1] to [4], having arginine (80), phenylalanine (147) and asparagine (171) as amino acids in the viral coat protein.

[6] A nucleic acid containing the nucleotide sequence of SEQ ID NO:1, SEQ ID NO:2, SEQ ID NO:4 or SEQ ID NO:5 or a nucleotide sequence complementary to the nucleotide sequence of SEQ ID NO:1, SEQ ID NO:2, SEQ ID NO:4 or SEQ ID NO:5 (with T being U in the nucleotide sequence when the nucleic acid is RNA).

[7] A method of controlling tomato yellow leaf curl disease using a yellow leaf curl disease tolerant tomato and the virus according to any one of [1] to [5].

[8] A method of preventing transmission of yellow leaf curl virus using a yellow leaf curl disease tolerant tomato and the virus according to any one of [1] to [5].

Advantageous Effects of Invention

A novel tomato yellow leaf curl virus that is not mediated by an insect vector can be provided by the present invention.

BRIEF DESCRIPTION OF DRAWINGS

FIG. 2 shows with underlines the amino acids in a TYLCV amino acid sequence that are different from those of other strains. Amino acids of isolates 17G, 10-1, mix8-2, Nagasaki, Omura (Eustoma), and Miyazaki are included as SEQ ID NOs:20-25.

FIG. 3 shows with underlines the amino acids in the amino acid sequence of the TYLVC Rep region that are different from those of other strains. Amino acids of isolates 17G, 10-1, mix8-2, Nagasaki, Omura (Eustoma), and Miyazaki are included as SEQ ID NOs:26-31.

FIG. 4 shows multiple sequence alignment results for the amino acid sequence of the CP region.

DESCRIPTION OF EMBODIMENTS

Figure 1:
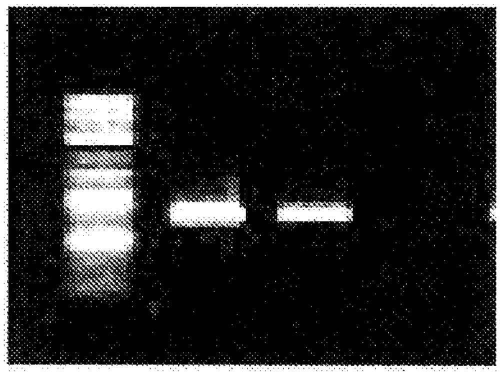
FIG. 1 shows the results of agarose gel electrophoresis in a TYLCV assay test.

Embodiments of the present invention are explained in detail below. The present invention is not limited to the following embodiments, and can be implemented with various modifications within the scope of its gist.

The present invention relates to a tomato yellow leaf curl virus that is a virus not mediated by an insect vector.

In the present invention, the term "tomato yellow leaf curl virus (TYLCV)" means a virus belonging to the genus Begomovirus in the Geminiviridae family, and having a single-segment genome of circular single-stranded DNA, with the viral particles being double particles comprising two linked spheres each 20 nm in diameter.

The TYLCV genome has sequences coding for MP, CP, REn, TrAP, Rep and C4 proteins, with CP being a coat protein that envelopes the DNA of the virus, and is therefore involved in virus infection and insect-borne transmission.

TYLCV occurs principally in the Middle East, North and Central America, Southeast Asia and East Asia (Japan and China). Primarily two strains of TYLCV occur in Japan: TYLCV Israel strain, which occurs in Kyushu and Kanto region (beginning with an isolated strain discovered in Nagasaki), and Israel mild strain, which occurs in Tokai and Kanto regions.

In the present invention, the term "insect vector" means an insect capable of transmitting a plant virus from one individual plant to another. The term "transmitting" a plant virus here means not only cases in which symptoms of viral infection appear in a plant in which the plant virus was not originally confirmed, but also cases in which infection of a plant by the plant virus can be confirmed by genetic analysis or the like even if the plant does not exhibit any symptoms.

In the present invention, as described in the examples, infection of a tomato by TYLCV can be verified by the TC-PCR method.

An example of an insect vector that transmits the tomato yellow leaf curl virus includes *Bemisia tabaci.*

Several types of *Bemisia tabaci* occur in Japan, but mainly there are two widespread types, the *Bemisia tabaci* biotype B (previously referred to as silverleaf whitefly; hereinafter occasionally referred to as "*Bemisia tabaci* B") and *Bemisia tabaci* Q.

Reports up to now have shown no difference in insect-mediation for transmitting TYLCV between *Bemisia tabaci* B and *Bemisia tabaci* Q (Kitamura et al., Proc. Kansai Pl. Prot. Vol. 51, pp. 81-83, 2009). *Bemisia tabaci* Q is more pesticide tolerant than *Bemisia tabaci* B.

TYLCV is transmitted by *Bemisia tabaci*. It can also be transmitted by grafting tomato plants infected with TYLCV, but is not transmitted by ovarian transmission, contact transmission, seed transmission, soil transmission, mechanical inoculation with infected leaf sap or the like.

Thus, transmission of TYLCV in tomatoes becomes a problem of transmission by insect vectors such as *Bemisia tabaci* in actual cultivation facilities, and a new method of controlling tomato yellow leaf curl disease could be provided if transmission by the insect vector could be controlled. A new control method is provided by the tomato yellow leaf curl virus discovered in the present invention, which is not transmitted by an insect vector.

In the present invention, the term "not transmitted by an insect vector (non insect-mediated)" means that a tomato yellow leaf curl virus is not transmitted by an insect vector from a tomato infected with a tomato yellow leaf curl virus to a tomato that is susceptible to a tomato yellow leaf curl virus but does not carry that virus (hereinafter occasionally referred to as "test tomato") during seedling period. Specifically, being non insect-mediated can be verified as follows. *Bemisia tabaci* that does not carry TYLCV is allowed to feed on a TYLCV-infected tomato, and is collected after it has fed. A test tomato plant is prepared in a separate isolation case, and said *Bemisia tabaci* is released inside said isolation case and allowed to feed on the test tomato. Said *Bemisia tabaci* is then collected and is confirmed to carry TYLCV, and while the test tomato is raised and the absence of TYLCV infection in the test tomato is confirmed during the seedling period.

The non insect-mediated tomato yellow leaf curl virus (non insect-mediated TYLCV) of the present invention is an virus that is obtainable by screening viruses that are not transmitted by an insect vector, by first allowing the insect vector to feed and then testing for transmission of the virus.

The non insect-mediated TYLCV of the present invention is preferably a virus having DNA represented by the nucleotide sequence of SEQ ID NO:1. It may also be a virus having DNA represented by the nucleotide sequence of SEQ ID NO:2, which is obtained as a chimera clone. In the present invention, such nucleotide sequence may include nucleotide sequences with substitutions, deletions, additions or the like in SEQ ID NO:1 and SEQ ID NO:2 as long as it is capable of encoding the necessary proteins encoded by the nucleotide sequences of SEQ ID NO:1 and SEQ ID NO:2 in the same way.

Because the non insect-mediated TYLCV of the present invention is not transmitted by an insect vector, a tomato carrying said non insect-mediated TYLCV has the advantage of not being a source of infection by a virus.

Moreover, the benefits of the non insect-mediated TYLCV of the present invention can be exploited to advantage in yellow leaf curl disease tolerant tomatoes.

In the present invention, the term "yellow leaf curl disease tolerant tomato" (hereinafter occasionally referred to as "tolerant tomato") means a tomato having a tolerant gene that cannot prevent TYLCV infection, but is capable of suppressing symptoms of tomato yellow leaf curl disease caused by TYLCV.

Examples of tolerant genes include Ty-1, Ty-2, Ty-3, Ty-3a, Ty-4 and Ty-5.

A tolerant tomato may be a tomato of a wild strain that has acquired a tolerant gene naturally, a tomato having a tolerant gene introduced by hybridization, or a tomato having a tolerant gene introduced by genetic recombination techniques.

Specific examples of tolerant tomatoes include TY Momotaro Sakura, TY Momotaro Arc, Shurei, TY Chie, TY Chika, AEGEAN. In a tolerant tomato, the tolerant gene may be introduced with homo- or hetero-zygous condition.

A tolerant tomato refers to one in which symptoms of tomato yellow leaf curl disease are absent or slight even with TYLCV infection due to the presence of a tolerant gene that can suppress symptoms of tomato leaf curl disease caused by TYLCV. Slight symptoms here refer to condition in that leaf size is normal, the leaf margins are slightly rounded, and the leaf color is green as usual. Severe symptoms refer to condition in that leaf becomes small, leaf tips are curled towards the back, and the leaf has turned yellow.

Because tolerant tomatoes may carry TYLCV even though symptoms of tomato yellow leaf curl disease are absent or slight, TYLCV can be transmitted from a tolerant tomato to another TYLCV-susceptible tomato by means of an insect vector if the tolerant tomato carries the TYLCV. Moreover, the fact that the symptoms of tomato yellow leaf curl disease are absent or slight in tolerant tomatoes makes it impossible to disrupt infection cycle of TYLCV by removing TYLCV-infected plants at an early stage.

Thus, TYLCV control methods using tolerant tomatoes may not be sufficiently effective with respect to TYLCV susceptible tomatoes.

When a tolerant tomato is infected with virulent TYLCV (TYLCV that produces severe symptoms in TYLCV susceptible tomatoes), even though the symptoms are generally absent or slight, the virulent TYLCV itself proliferates inside the tomato body, and if an insect vector such as *Bemisia tabaci* visits the plant, it can transmit the virulent TYLCV to another tomato.

That is, the plant may become a source of contamination for secondary TYLCV infection, and this has delayed the adoption of tolerant tomatoes. If tolerant tomatoes are inoculated in advance with the non insect-mediated TYLCV of the present invention, however, at least this non insect-mediated TYLCV will not be transmitted to other tomatoes.

Moreover, although the mechanism is unknown, the present invention provide a advantageous effect that if a tolerant tomato is inoculated in advance with non insect-mediated TYLCV, even if a *Bemisia tabaci* insect vector carrying virulent insect-mediated TYLCV subsequently comes into contact with the tolerant tomato that has been inoculated in advance with the non insect-mediated TYLCV, the virulent insect-mediated TYLCV carried by said *Bemisia tabaci* will not infect the tolerant tomato that has been inoculated with the non insect-mediated TYLCV, and will not be secondarily transmitted by insect-mediation from the tolerant tomato that has been inoculated with the non insect-mediated TYLCV to another TYLCV susceptible tomato.

The non insect-mediated TYLCV of the present invention is a novel and superior virus that can compensate for the weakness of tolerant tomatoes, namely that they are a "source of contamination for secondary infection", and that can provide a new control method as a method of controlling plant viruses. The present invention also provides a combination of non insect-mediated TYLCV with a tolerant tomato.

With the non insect-mediated TYLCV of the present invention, it is possible to reduce the use of pesticides and the use of materials to prevent physical incursion when cultivating tolerant tomatoes, allowing tomatoes to be cultivated safely and with less labor. It is also expected that by cultivating a certain number of tolerant tomatoes infected with the non insect-mediated TYLCV of the present invention, it will be possible to effectively prevent the spread of TYLCV in that region. Moreover, if the tomatoes inoculated with the non insect-mediated TYLCV of the present invention are tolerant tomatoes, fruit yields will be little affected because symptoms of non insect-mediated TYLCV are absent or slight. In addition, because the non insect-mediated TYLCV of the present invention is not transmitted by an insect vector, it will not be transmitted to other tomatoes and cause symptoms of TYLCV infection.

Thus, TYLCV that is not transmitted by an insect vector is a novel virus, and the effect of preventing virulent TYLCV transmission in tolerant tomatoes is one that has not been achieved in the past.

The present invention also provides a nucleic acid containing the nucleotide sequence of SEQ ID NO:1, which is isolated from the non insect-mediated virus. The present invention also provides a nucleic acid containing the nucleotide sequence of SEQ ID NO:2, which is isolated from a chimera clone.

The present invention also provides nucleic acids containing SEQ ID NO:4 encoding CP as a partial sequence in the nucleotide sequence of SEQ ID NO:1 and SEQ ID NO:5 encoding CP as a partial sequence in the nucleotide sequence of SEQ ID NO:2.

The claimed nucleotide sequences of the nucleic acids of the present invention may be nucleotide sequences having one or more nucleotides deleted, added and/or substituted therein to the extent that this is not contrary to the gist of the present invention, and are preferably DNA having the nucleotide sequences of SEQ ID NO:1, SEQ ID NO:2, SEQ ID NO:4 or SEQ ID NO:5. When these nucleic acids are RNA, however T (thymine, shown as t in the sequence tables) becomes U (uracil) in SEQ ID NO:1, SEQ ID NO:2, SEQ ID NO:4 and SEQ ID NO:5. Apart from ATGCU, bases that are equivalent to ATGCU may also be included in the nucleotide sequences represented by SEQ ID NO:1, SEQ ID NO:2, SEQ ID NO:4 and SEQ ID NO:5, and equivalent bases may include those obtained by substituting or modifying the base part of ATGCU. The sugar part of the nucleic acid may also be substituted or modified as long as it is equivalent to ribose or deoxyribose.

The present invention also provides nucleic acids containing nucleotide sequences complementary to the nucleotide sequences of SEQ ID NO:1, SEQ ID NO:2, SEQ ID NO:4 and SEQ ID NO:5. Although the nucleotide sequences of these nucleic acids are nucleotide sequences complementary to the nucleotide sequences of SEQ ID NO:1, SEQ ID NO:2, SEQ ID NO:4 and SEQ ID NO:5, they may be nucleotide sequences having one or more nucleotides deleted, added and/or substituted therein to the extent that this is not contrary to the gist of the present invention, and are preferably DNA or RNA having nucleotide sequences complementary to the nucleotide sequences of SEQ ID NO:1, SEQ ID NO:2, SEQ ID NO:4 and SEQ ID NO:5.

The nucleotide sequence of SEQ ID NO:1 corresponds to the entire base sequence of the isolated strain 17G. The nucleotide sequence of SEQ ID NO:2 corresponds to the entire base sequence of the chimera clone. The chimera clone, which is described in detail in the examples, comprises the entire base sequence (SEQ ID NO:3) of ISR10-1, isolated as the TYLCV Israel Kumamoto virulent isolated strain from a farm in Kumamoto Prefecture, with mutations that change the A of base No. 705 to G, the A of base No. 906 to T and the G of base No. 979 to T.

When used in combination with a tolerant tomato, the non insect-mediated TYLCV of the present invention can prevent the tolerant tomato from becoming a source of TYLCV infection, and prevent secondary TYLCV infection of TYLCV susceptible tomatoes from tolerant tomatoes. Moreover, a tolerant tomato that has been infected in advance with non insect-mediated TYLCV does not become a source of further infection by virulent insect-mediated TYLCV even when subsequently exposed to virulent insect-mediated TYLCV, thereby preventing the occurrence of tomato yellow leaf curl disease in TYLCV susceptible tomatoes.

Non insect-mediated TYLCV is maintained by grafting or by propagation by cuttings. Graft inoculation of tomatoes with non insect-mediated TYLCV can be accomplished at any stage of tomato growth, but is preferably done after 2 to 6 true leaves have appeared in order to achieve efficient grafting and subsequent infection with the non insect-mediated TYLCV.

A lateral shoot can be used as tomatoes infected with non insect-mediated TYLCV, and the presence of the virus was satisfactorily confirmed in the lateral shoot with two true leaves or more.

EXAMPLES

The present invention is explained in more detail below using examples, but the scope of the invention is not limited to these examples.

<Maintenance Control of TYLCV>

The tomato yellow leaf curl virus (TYLCV) used in the examples was a virus isolated in Kumamoto Prefecture. Maintenance control of TYLCV was accomplished by infecting tomatoes (House Momotaro, Reiyo, Shurei, etc.) with the isolated TYLCV and keeping then in an environment of 10 to 30° C. Successive generations of TYLCV were obtained by successively propagating lateral shoots (side shoots) of the tomatoes infected with TYLCV.

<Testing for TYLCV>

DNA was extracted by the tube capture (hereinafter referred to as "TC") method as an easy DNA extraction method. PCR was performed with the extracted DNA as a template to verify whether or not a plant was infected with TYLCV. Specifically, the TC-PCR method was performed as follows.

First, 100 mg to 1 g of TYLCV infected leaves were prepared, and ground in 5 to 20 times of its volume of extraction buffer (0.05 M carboxylic acid buffer, 0.01M phosphate buffer or 0.01M TRIS buffer). 1.5 mL of the sap was placed in a microtube, and kept for 30 minutes to overnight at 4° C. to room temperature. The sap in the microtube was discarded, and the tube was rinsed with TE buffer (0.01M TRIS, 0.001M EDTA) or 0.01M phosphate buffer or the like, after which sterile water was added to obtain a TYLCV DNA extract.

One μL of this DNA extract was taken and subjected to PCR in accordance with the methods of a Promega GoTaq® Green Master Mix. PCR was performed in 35 cycles each consisting of 50 seconds at 95° C., 50 seconds at 56° C. and 45 seconds at 72° C. using the primers:

```
TYPRB2F:                        (SEQ ID NO: 10)
5'CCCTCTGGAATGAAGGAACA
and

TYC-R:                          (SEQ ID NO: 11)
5'-TTGAAAAATTGGRCTCTCAA,
```

which are matched to regions that are relatively stable among isolated strains of TYLCV, to thereby amplify the target region. Following PCR, the target DNA was confirmed by 1.2% agarose gel electrophoresis. The results are shown in FIG. 1.

<Selection and Stability Confirmation of Non Insect-Mediated TYLCV>

A virus-free TYLCV-susceptible tomato variety (House Momotaro, Takii & Co., Ltd.) was infected by graft inoculation with several isolated strains of TYLCV that were isolated in Kumamoto Prefecture and were confirmed by agarose gel electrophoresis to have infected tomatoes.

After TC-PCR to confirm that each isolated strain had thoroughly infected the susceptible tomato, the tomatoes were placed individually in isolation cases, and hundreds of virus-free *Bemisia tabaci* B (obtained in Chiba Prefecture) were released and allowed to feed for 3 days.

Next, *Bemisia tabaci* B were collected, each of 10 new virus-free TYLCV-susceptible tomatoes (House Momotaro, hereinafter occasionally referred to as "test tomato") were separately placed in the isolation case, and 10 to 20 of the *Bemisia tabaci* B were released per test tomato. After being allowed to feed for 3 days, the *Bemisia tabaci* B were collected. After collection, the test tomatoes were raised for 45 days. The presence or absence of TYLCV transmission was verified by TC-PCR three times during the raising period for each of the 10 test tomatoes.

The same experiment was performed using a TYLCV Israel Kumamoto virulent isolated strain (hereinafter referred to as "TYLCV-Isr") as a control test. The results are shown in Table 1. Data for some of the isolated strains is given for the isolated strain group.

TABLE 1

| | Isolated strain group | | | | | Control test group TYLCV-Isr |
|---|---|---|---|---|---|---|
| | 17G | 21G | 30G | 48G | 76G | group |
| Number of transmission (plants/plants) | 0/10 | 10/10 | 10/10 | 9/10 | 7/10 | 18/20 |
| Transmission rate (%) | 0 | 100 | 100 | 90 | 70 | 90 |

As a result, while the transmission rate of TYLCV was 90% in the control test group, in the case of 17G of the isolated strain group all of the 10 test tomatoes were TYLCV negative (infection rate 0%), showing that 17G TYLCV was not transmitted at all by *Bemisia tabaci* B.

To verify the stability of the non insect-mediated TYLCV obtained from 17G, lateral shoots were taken from one 17G infected susceptible tomato and planted to propagate 8 tomato plants over the course of 5 months, and the non insect-mediation of each was evaluated in the same way by TC-PCR. The results are shown in Table 2.

TABLE 2

| | Isolated strain (17G) group | | | | | | | | Control test group TYLCV-Isr |
|---|---|---|---|---|---|---|---|---|---|
| | (1) | (2) | (3) | (4) | (5) | (6) | (7) | (8) | group |
| Transmission number (plants/plants) | 0/10 | 0/10 | 0/10 | 0/10 | 0/10 | 0/10 | 0/10 | 0/10 | 18/20 |
| Transmission rate (%) | 0 | 0 | 0 | 0 | 0 | 0 | 0 | 0 | 90 |

As a result, none of 17G derived from the above 8 tomato plants infected with 17G and propagated separately was transmitted by *Bemisia tabaci* B. Thus, 17G retained stably non insect-mediation even after 5 months during which the tomatoes were divided by cutting propagation.

A total of 90 test tomatoes were used in all the 17G TYLCV insect-mediation evaluation tests, and the 17G TYLCV was not insect-mediated by *Bemisia tabaci* in any of the 90 tomatoes (transmission rate: 0%=0/90). Such non insect-mediated TYLCV has not previous been reported, and has now been obtained for the first time anywhere in the world.

The entire DNA sequence of the resulting 17G non insect-mediated TYLCV was inserted into a pCAMBIA2300 (Cambia Co.) *agrobacterium* binary vector, and was accepted as a plasmid (pCAM17G1) on Nov. 2, 2010 by the National Institute of Advanced Industrial Science and Technology International Patent Organism Depositary, assigned the Receipt No. FERM-AP22037, and assigned the Accession No. FERM P-22037 on Dec. 3, 2010.

The plasmid (pCAM17G1) was prepared specifically as follows.

Because TYLCV is a circular single-stranded DNA virus, at least 2 of IR region (bases No. 1 to 306) in the TYLCV genome must be inserted into a plasmid when constructing an infectious clone plasmid. We therefore adopted the method of placing one additional IR region at the end of the full-length sequence.

As shown by SEQ ID NO:1, 17G non insect-mediated TYLCV has 2774 bases in the form of single-stranded circular DNA with base No. 1 and base No. 2774 linked together. To construct a 17G infectious clone plasmid, bases Nos. 2769 (passing through 2774/1) to 1187 were amplified by PCR using 17G DNA as the template.

PCR was performed using a forward primer comprising a HindIII restriction enzyme site added to the No. 2769 side:

```
TY-1F-HIN:                    (SEQ ID NO: 12)
5'-TATAAGCTTAGGCATGTTGAAATGAATCGG,
```

and a reverse primer containing a SphI restriction enzyme site:

```
TY-1R-SPH:                    (SEQ ID NO: 13)
5'-GATTAGAGGCATGCGTACATG.
```

The resulting PCR amplified product was cleaved with the restriction enzymes HindIII and SphI, to obtain a DNA fragment having an IR region at the forward side (hereinafter referred to as "DNA fragment A"). The DNA fragment A was inserted into the HindIII and SphI cleavage sites of a pUC19 cloning vector (hereinafter referred to as "Clone 1").

Next, to prepare a DNA fragment having an IR region at the backward side (hereinafter referred to as "DNA fragment B"), bases No. 1170 to 334 (passing through 2774/1) were amplified by PCR using 17G viral DNA as the template.

PCR was performed using a forward primer containing a SphI restriction enzyme site:

```
TY-2F-SPH:                    (SEQ ID NO: 14)
5'-GTACGCATGCCTCTAATCCAG,
```

and a reverse primer comprising a BamHI site added to the No. 334 side:

```
TY-2R-BAM:                    (SEQ ID NO: 15)
5'-ATGGATCCGAAACTCATTAAGAAGTGGGTC.
```

The resulting PCR amplified product was cleaved with the restriction enzymes SphI and BamHI, to obtain a DNA fragment B. The DNA fragment B was inserted into the SphI and BamHI cleavage sites of the Clone 1 (hereinafter referred to as the "Clone 2").

As a result, a (roughly 3.1 kb) sequence was inserted between the HindIII and BamHI cleavage sites of the Clone 2, comprising DNA fragments A and B linked together, and consisting of bases Nos. 2769 to 2774, 1 to 2774 and an additional 1 to 334 to thereby provide an additional IR region at the backward side of the full-length sequence.

Next, the Clone 2 was treated with the restriction enzymes HindIII and BamHI to excise the roughly 3.1 kb DNA fragment. The excised DNA fragment was inserted into the *agrobacterium* binary vector pCAMBIA2300 (Cambia Co.), to obtain a 17G infectious clone plasmid (pCAM17G1) (accession No. FERM P22037).

The plasmid "pCAM17G1" was assigned the Receipt No. FERM-AP22037 on Dec. 3, 2010 upon domestic deposit at the National Institute of Advanced Industrial Science and Technology International Patent Organism Depositary (Central 6, 1-1 Higashi 1-chome, Tsukuba-shi, Ibaraki Prefecture, Japan), and based on FERM P-22037 deposited on Nov. 2, 2010 (domestic receipt date), a transfer request was then accepted for deposit based on the Budapest Treaty on the International Recognition of the Deposit of Microorganisms for the Purposes of Patent Procedure, and on Jan. 20, 2012 the plasmid was assigned the receipt number "FERM BP-11450" for international accession based on the Budapest Treaty on the International Recognition of the Deposit of Microorganisms for the Purposes of Patent Procedure.

Plants were infected with this plasmid by the agroinfiltration method, the virus was expressed, and retention of non insect-mediation was confirmed.

The agroinfiltration method is explained below. The plasmid (pCAM17G1) was mixed with *Agrobacterium tumefacience*, and the mixture was immersed for 5 minutes in a 37° C. water bath to introduce the plasmid into the *agrobacterium*. This was then cultured on LB agar medium containing kanamycin, and the resulting colony was cultured in LB liquid medium, and centrifuged. The precipitate was shaken in LB liquid medium containing kanamycin, and the resulting suspension containing cell bodies was injected with a syringe into two tomato leaves, 0.5 mL per leaf, to infect the tomato with 17G. This tomato was cultivated in an growth chamber for 2 weeks (25° C. constant, 16/8 hour light/dark cycle), and the virus was detected. *Bemisia tabaci* were allowed to feed on the tomato, and the same *Bemisia tabaci* were then allowed to feed on a virus-free test tomato to confirm retention of non insect-mediation. This plasmid and 17G have been maintained in storage by the applicants, and furnishings in accordance with the provisions of Article 27(3) of the Japanese Patent Law Enforcement Regulations are guaranteed by the applicants.

The nucleotide sequence inserted into the deposited plasmid is the nucleotide sequence represented by SEQ ID NO:1. Being an infectious clone plasmid, a sequence consisting of bases Nos. 2769 to 2774, 1 to 2774 and 1 to 334 linked together to thereby provide an additional IR region at the backward side of the full-length DNA represented by SEQ ID NO:1 has been inserted into the plasmid.

<Nucleotide Sequence of Non Insect-Mediated TYLCV>

The nucleotide sequence of 17G non insect-mediated TYLCV was determined (SEQ ID NO:1) with a direct sequencing kit (Applied Biosystem "BigDye Terminator v3.1 Cycle Sequencing Kit") and a "3500 Genetic Analyzer" sequencer, using a combination of the primers UPV1

```
                                    SEQ ID NO: 16)
(KSGGGTCGACGTCATCAATGACGTTRTAC:
and

PAV1c715                            SEQ ID NO: 17)
(GATTTCTGCAGTTDATRTTYTCRTCCATCCA:

and a combination of
the primers TY-ext01                SEQ ID NO: 18)
(AGTATTGTCATTGAGGGTGATAGCAG:
and

TY-ext02                            SEQ ID NO: 19)
(GCCCATGTAAAGTCCAGTCTTATGAGC:.
```

<Non Insect-Mediated TYLCV can Prevent Secondary Transmission of Virulent TYLCV>

Virus-free tolerant tomatoes were infected with the 17G non insect-mediated TYLCV by grafting.

The presence of TYLCV in the plant bodies of the tolerant tomatoes was confirmed by TC-PCR.

Next, 200 of *Bemisia tabaci* B that had previously acquired TYLCV-Isr from separately-prepared TYLCV-Isr infected tomatoes were released for 5 days with the 17G infected tolerant tomatoes (this treatment is referred to as challenge inoculation).

Next, the *Bemisia tabaci* B was collected, and 8 weeks after the challenge inoculation, virus-free *Bemisia tabaci* B was released with the 17G infected tolerant tomatoes and allowed to feed for 5 days, after which the *Bemisia tabaci* B was collected and released for 5 days 20 of the *Bemisia tabaci* B per plant with 20 virus-free susceptible tomatoes (this treatment is referred to secondary transmission).

After 5 days, the *Bemisia tabaci* B was killed, the susceptible tomatoes were grown for 35 days, and TYLCV infection was investigated by TC-PCR.

As a control test group, challenge inoculation of virus-free tolerant tomatoes by TYLCV-Isr was performed without infecting the tomatoes with 17G non insect-mediated TYLCV. The results are shown in Table 3.

TABLE 3

| | 17G group | Control test group (untreated) |
|---|---|---|
| Transmission number (plants/plants) | 0/36 | 34/36 |
| Secondary transmission rate (%) | 0 | 94.4 |

When the susceptible tomatoes were analyzed after having been grown for 35 days following secondary transmission, the transmission rate was 94.4% (34/36) in the control group, but in the 17G group there was absolutely no TYLCV-Isr transmission, with all the plants testing negative for an transmission rate of 0% (0/36). This shows that when tolerant tomatoes are infected in advance with the 17G isolated strain, they are not subsequently infected by insect-mediated virulent TYLCV even when *Bemisia tabaci* carrying the insect-mediated virulent TYLCV are brought into contact with and allowed to feed on the infected tolerant tomatoes infected in advance with the 17G, nor is there any secondary transmission of the insect-mediated virulent TYLCV to other virus-free susceptible tomatoes.

As mentioned above, with TYLCV, interference such as prevention of transmission of other insect-mediated TYLCV has not been reported before.

<Preparation of Insect-Mediated Clone Plasmid>

An insect-mediated ISR10-1 infectious clone plasmid was prepared by methods similar to those used in preparing the 17G non insect-mediated TYLCV infectious clone plasmid except that pR1909 (Takara Bio) was used as the *agrobacterium* binary vector.

Using the isolated strain TYLCV-Isr (ISR10-1), which was isolated from tomatoes on a farm in Kumamoto Prefecture and has been confirmed to be insect-mediated, a roughly 3.1 kb DNA fragment consisting of the string of bases Nos. 2769 to 2774, 1 to 2774 and an additional 1 to 334 of ISR10-1 was inserted into the HindIII and BamHI cleavage sites of the *agrobacterium* binary vector pR1909 (Takara Bio) to obtain an ISR10-1 infectious clone plasmid.

<Preparation of Chimera Clone Plasmid>

Synthetic DNA comprising HindIII and SphI sites added to the termini of synthetic DNA homologous to the sequence from the HindIII site to base No. 1178 (SphI site) of the ISR10-1 infectious clone plasmid, and having G substituted for the A of base No. 705, T for the A of base No. 906 and T for the G of base No. 979, was cleaved with the restriction enzymes HindIII and SphI, and inserted into the HindIII and SphI cleavage sites of the ISR10-1 infectious clone plasmid to prepare a chimera clone plasmid.

That is, the chimera clone had substitutions for three amino acids of the coat protein (CP) of the insect-mediated ISR10-1, namely, arginine (CGA) substituted for the No. 80 glutamine (CAA), phenylalanine (TTT) for the No. 147 tyrosine (TAT), and asparagine (AAT) for the No. 171 lysine (AAG).

The resulting chimera clone plasmid was deposited internationally as pRI-ISR10-1chimera705-906-979 based on the Budapest Treaty on the International Recognition of the Deposit of Microorganisms for the Purposes of Patent Procedure, received at the National Institute of Advanced Industrial Science and Technology International Patent Organism Depositary (Central 6, 1-1 Higashi 1-chome, Tsukuba-shi, Ibaraki Prefecture, Japan) on Jan. 30, 2012, and assigned the Receipt No. FERM ABP-11465.

<Non Insect-Mediation of Chimera Clone>

Tomatoes were inoculated with the resulting chimera clone plasmid by the agroinfiltration method using techniques similar to those described above, and non insect-mediation was confirmed as follows.

Three weeks after inoculation with the chimera clone plasmid, systemic infection was confirmed by TC-PCR. Those chimera clone-infected tomatoes that were confirmed to be systemically infected (virus acquisition source) were placed in isolation cases, and 300 to 400 virus-free *Bemisia tabaci* Q were released and allowed to acquisition feed for 5 days.

The *Bemisia tabaci* Q acquired the chimera clone were collected, each of 10 new test tomatoes was separately prepared in isolation case, and 20 to 30 of *Bemisia tabaci* Q were released per test tomato. These were allowed to feed for 5 days, and the *Bemisia tabaci* Q was collected and killed. After collection, the test tomatoes were raised for 35 days. During the raising period, each of the 10 tomatoes was checked 3 times by TC-PCR for transmission by the chimera clone.

As a control test group, tomatoes infected with insect-mediated ISR10-1 were used as the virus acquisition source in a similar test. The results are shown in Table 4.

TABLE 4

| | Chimera clone inoculation group | Control test group ISR10-1 |
|---|---|---|
| Transmission number (plants/plants) | 0/10 | 10/10 |
| Transmission rate (%) | 0 | 100 |

As a result, while all 10 of the tomatoes in the control test group were TYLCV positive, for the transmission rate of 100% (10/10), in the chimera clone inoculation group all of the 10 test tomatoes were TYLCV negative (0/10), showing that the chimera clone having three amino acid residues peculiar to non insect-mediated TYLCV substituted in the CP gene coding region of TYLCV is not transmitted at all by *Bemisia tabaci* Q.

This shows that the insect-mediation of insect-mediated ISR10-1 is eliminated by substituting three residues in the CP gene coding region of TYLCV, namely arginine for the No. 80 glutamine, phenylalanine for the No. 147 tyrosine and asparagine for the No. 171 lysine, so it can be seen that these sites are involved in non insect-mediation.

*Bemisia tabaci* was applied to tomatoes infected with insect-mediated ISR10-1 and the chimera clone, and allowed to acquisition feed for 5 days, 10 of *Bemisia tabaci* were sampled randomly from each tomato after 3 days of acquisition feeding, and the virus retention rates were investigated. As a result, it was found that 10/10 (100%) of the *Bemisia tabaci* still carried TYLCV in all cases.

<Relationship Between CP Region Mutations and Non Insect-Mediation>

When the nucleotide sequences of the CP regions of Geminiviridae including TYLCV recorded in GenBank, EMBL, DDBJ and PDB, specifically the Nagasaki strain, Omura (Eustoma) strain, Miyazaki strain, mix8-2 strain (an insect-mediated clone isolated as an Israel strain other than ISR10-1) and ISR10-1, were compared with the CP region of the non insect-mediated 17G, it was shown that the amino acids Nos. 80, 147 and 171 mentioned above were peculiar to 17G alone (FIG. 2, FIG. 3). In FIG. 2, the amino acids that are different from those of other strains are shown with underlines.

In general, these Geminiviridae viruses are reported to be insect-transmitted, and this suggests that amino acid mutations of the CP region are involved in non insect-mediation.

There appears to be a very close association between mutations of the CP region and non insect-mediation of TYLCV, and it has been confirmed that insect-mediated TYLCV strain can be converted to non insect-mediated by substituting amino acids of the CP region. FIG. 4 shows the results of multiple sequencing alignment of the amino acid sequences of the CP regions of 17G, ISR10-1 and the chimera clone.

As discussed above, in the present invention, since it appears that three amino acids of the CP region of TYLCV are involved in insect-mediation, it was thought that TYLCV comprising the DNA represented by the nucleotide sequences of SEQ ID NO:4 and SEQ ID NO:5 encoding the CP region would have the property of non insect-mediation, and that TYLCV having a peptide with an amino acid sequence represented by SEQ ID NO:7 or SEQ ID NO:8 would also have the property of non insect-mediation.

TYLCV having a peptide with an amino acid sequence represented by SEQ ID NO:7 or SEQ ID NO:8 with one or more amino acids deleted, added and/or substituted therein is also included in the scope of the present invention as long as TYLCV having the property of non insect-mediation can be provided thereby.

Moreover, TYLCV having arginine (80), phenylalanine (147) and asparagine (171) as amino acids of the coat protein (CP) is also included in the scope of the present invention as a non insect-mediated virus. These three amino acids do not necessarily have to be located exactly at the Nos. 80, 147 and 171 positions of the CP region, and a virus having an amino acid sequence in which the corresponding amino acids are arginine, phenylalanine and asparagine when aligned by known methods by a person skilled in the art is also included in the scope of the present invention. Moreover, structurally similar amino acids may also be substituted for the arginine (80), phenylalanine (147) and asparagine (171) as long as the function of non insect-mediation retained in the virus. The arginine (80), phenylalanine (147) and asparagine (171) are described as R80, F147 and N171 using single-letter nomenclature. In the present invention, TYLCV having the three amino acids R80, F147 and N171 in the coat protein is a non insect-mediated virus as long as the function of the coat protein is not lost. In the present invention, non insect-mediated TYLCV having arginine (80), phenylalanine (147) and asparagine (171) as amino acids in the viral coat protein may be a virus having R80, F147 and N171 as mutations corresponding to Q80R, Y147F and K171N in the CP protein of insect-mediated TYLCV, or may be a virus that is not derived from insect-mediated TYLCV having Q80, Y147 and K171 exactly, but in which the corresponding amino acids are arginine, phenylalanine and asparagine as a result of alignment.

CROSS-REFERENCE TO RELATED APPLICATIONS

The present application is based on a Japanese Patent Application submitted on Feb. 4, 2011 (Japanese Patent Application No. 2011-023199), the content of which is herein incorporated by reference

SEQUENCE TABLE FREE TEXT

SEQ ID NO: 1 shows the entire nucleotide sequence of the isolated strain 17G.

SEQ ID NO: 2 shows the entire nucleotide sequence of a non insect-mediated chimera clone obtained from TYLCV-Isr (ISR10-1).

SEQ ID NO: 3 shows the entire nucleotide sequence of TYLCV-Isr (ISR10-1).

SEQ ID NO: 4 shows the entire nucleotide sequence of the CP region of the isolated strain 17G.

SEQ ID NO: 5 shows the entire nucleotide sequence of the CP region of a non insect-mediated chimera clone obtained from TYLCV-Isr (ISR10-1).

SEQ ID NO: 6 shows the entire nucleotide sequence of the CP region of TYLCV-Isr (ISR10-1).

SEQ ID NO: 7 shows the amino acid sequence of the CP region of the isolated strain 17G.

SEQ ID NO: 8 shows the amino acid sequence of the CP region of a non insect-mediated chimera clone obtained from TYLCV-Isr (ISR10-1).

SEQ ID NO: 9 shows the amino acid sequence of the CP region of TYLCV-Isr (ISR10-1).

SEQ ID NO: 10 shows the nucleotide sequence of the TC-PCR primer TYPRB2F used in an assay test of TYLCY. SEQ ID NO:2 corresponds to bases Nos. 1040 to 1059 of TYLCV-Ng (Nagasaki strain).

SEQ ID NO: 11 shows the nucleotide sequence of the TC-PCR primer TYC-R used in an assay test of TYLCY. SEQ ID NO: corresponds to bases Nos. 1814 to 1796 of TYLCV-Ng.

SEQ ID NO: 12 shows the nucleotide sequence of the forward primer TY-1F-HIN, corresponding to bases Nos. 2769 to 15 of 170 with the HindIII sequence added to the 5' side, which was used to amplify bases 2769 to 1187 by PCR using viral DNA of 17G as the template.

SEQ ID NO: 13 shows the nucleotide sequence of the reverse primer TY-1R-SPH, corresponding to bases Nos. 1187 to 1167 of 170, which was used to amplify bases 2769 to 1187 by PCR using viral DNA of 170 as the template.

SEQ ID NO: 14 shows the nucleotide sequence of the forward primer TY-2F-SPH, corresponding to bases Nos. 1170 to 1190 of 170, which was used to amplify bases 1170 to 334 by PCR using viral DNA of 17G as the template.

SEQ ID NO: 15 shows the nucleotide sequence of the reverse primer TY-2R-BANS, corresponding to bases Nos. 334 to 313 of 170 with the BamHI sequence added to the 5' side, which was used to amplify bases 1170 to 334 by PCR using viral DNA of 170 as the template.

SEQ ID NO: 16 shows the nucleotide sequence of primer UPV1 used in determining the nucleotide sequence of the non insect-mediated TYLCV.

SEQ ID NO: 17 shows the nucleotide sequence of the primer PAV1c715 used in determining the nucleotide sequence of the non insect-mediated TYLCV.

SEQ ID NO: 18 shows the nucleotide sequence of the primer TY-ext01 used in determining the nucleotide sequence of the non insect-mediated TYLCV.

SEQ ID NO: 19 shows the nucleotide sequence of the primer TY-ext02 used in determining the nucleotide sequence of the non insect-mediated TYLCV.

The invention claimed is:

1. A tomato yellow leaf curl virus not transmitted by an insect vector, wherein said virus comprises the nucleotide sequence of SEQ ID NO:2.

2. The virus according to claim 1, wherein the insect vector is whitefly *Bemisia tabaci* (Gennadius).

3. A nucleic acid containing the nucleotide sequence of SEQ ID NO:2 or SEQ ID NO:5.

4. A method of controlling tomato yellow leaf curl disease by inoculating a yellow leaf curl disease tolerant tomato with the virus according to claim 1.

5. A method of preventing transmission of yellow leaf curl virus by inoculating a yellow leaf curl disease tolerant tomato with the virus according to claim 1.

6. An isolated plasmid comprising the nucleotide sequence of SEQ ID NO:4.

7. The isolated plasmid of claim 6, wherein said isolated plasmid encodes the polypeptide sequence of SEQ ID NO:7.

8. An isolated plasmid deposited at the National Institute of Advanced Industrial Science and Technology International Patent Organism Depository, Central 6, 1-1 Higashi 1-chome, Tsukuba-shi, Ibaraki Prefecture, Japan, said isolated plasmid having the deposit number of FERM BP-11450.

9. An isolated plasmid comprising the nucleic acid of claim 3.

10. An isolated plasmid comprising the nucleic acid of claim 3, wherein the nucleic acid contains the nucleotide sequence of SEQ ID NO:2.

11. An isolated plasmid comprising the nucleic acid of claim 3, wherein the nucleic acid contains the nucleotide sequence of SEQ ID NO:5.

* * * * *

SEQUENCE LISTING

```
<160> NUMBER OF SEQ ID NOS: 31

<210> SEQ ID NO 1
<211> LENGTH: 2774
<212> TYPE: DNA
<213> ORGANISM: tomato yellow leaf curl virus

<400> SEQUENCE: 1

gttgaaatga atcggtgtcc ctcaaagctc tatggcaatc ggtgtatcgg tgtcttattt     60

atacctggac acctaatggt tatttggtaa tttcatgaat gttcatttta attcaaaatt    120

caaaaatcaa atcattaaag cggccatccg tataatatta ccggatggcc gcgccttttg    180

cttttatgtg gtccccacga gggttacaca gacgtcactg tcaaccaatc aaattgcatc    240

ctcaaacgtt agataagtct tcatttgtct ttatatactt ggtccccaag ttttttgtct    300

tgcaatatgt gggacccact tcttaatgag tttcctgaat ctgttcacgg atttcgttgt    360

atggtagcta ttaaatattt acagtccgtt gaggaaactt acgagcccaa tacattgggc    420

cacgatttaa ttagggatct tatatctgtt gtaagggccc gtgactatgt cgaagcgacc    480

aggcgatata atcatttcca cgcccgtctc gaaggttcgc cgaaggctga acttcgacag    540

cccatacagc agccgtgctg ctgtccccat tgtccaaggc acaaacaagc gacgatcatg    600

gacgtacagg cccatgtacc gaaagcccag aatatacaga atgtatcgaa gccctgatgt    660

tccccgtgga tgtgaaggcc catgtaaagt ccagtcttat gagcgacggg atgatattaa    720
```

-continued

```
gcatactggt attgttcgtt gtgttagtga tgttactcgt ggatctggaa ttactcacag    780

agtgggtaag aggttctgtg ttaaatcgat atatttttta gggaaagtct ggatggatga    840

aaatatcaag aagcagaatc atactaatca ggtcatgttc ttcttagtcc gtgatagaag    900

gccctttgga agcagcccaa tggattttgg acaggttttt aatatgttcg ataatgagcc    960

cagtaccgca accgtgaata atgatttgcg ggataggttt caagtgatga ggaaatttca   1020

tgctacagtt attggtggac cctctggaat gaaggaacag gcattagtta agagattttt   1080

taaaattaac agtcatgtaa cttataatca tcaggaggca gccaagtacg agaaccatac   1140

tgaaaacgcc ttgttattgt atatggcatg tacgcatgcc tctaatccag tgtatgcaac   1200

tatgaaaata cgcatctatt tctatgattc aatatcaaat taataaaatt tatattttat   1260

atcatgagtt tctgttacat ttattgtgtt ttcaagtaca tcatacaata catgatcaac   1320

tgatctgatt acattgttaa tggaaattac accaagacta tctaaatact taagaacttc   1380

atatctaaat actcttaaga aatgaccagt ctgaggctgt aatgtcgtcc aaattcggaa   1440

gttgagaaaa catttgtgaa tccccatgac cttcctgatg ttgtggttga atcttatctg   1500

aatggaaatg atgtcgtggt tcatttgaaa tggcctctgg ctgtgttctg ttatcttgaa   1560

atagagggga ttgtttatct cccagataaa aacgccattc tctgcctgag gagcagtgat   1620

gagttcccct gtgcgtgaat ccatgattat tgcagttgag gtggaggtag tatgagcagc   1680

cacagtctag gtctacacgc ttacgcctta ttggtttctt cttggctatc ttgtgttgga   1740

ccttgattga tacttgagaa cagtggctcg tagagggtga cgaaggttgc attcttgaga   1800

gtccaatttt tcaaggatat gttttttttct tcgtctagat attccctata tgaggaggta   1860

ggtcctggat tgcagaggaa gatagtggga attcccccctt taatttgaat gggcttcccg   1920

tactttgtgt tgctttgcca gtccctttgg gcccccatga attccttgaa gtgctttaaa   1980

taatgcgggt ctacgtcatc aatgacgttg taccacgcat cattactgta cacctttggg   2040

cttaggtcta gatgtccaca taaataatta tgtgggccta gagacctggc ccacattgtt   2100

ttccctgttc tgctatcacc ctcaacgaca atactcatgg gtctccatgg ccgcgcagcg   2160

gaagacacga cgttctcggc gacccactct tcaagttcat ctggaacttg attaaaagaa   2220

gaagaaagaa atggagaaac ataaacttct aatggaggac taaaaatcct atctaaattt   2280

gaatttaaat tatgaaattg taaaatataa tcctttgggg ccttctcttt taatatattg   2340

agggcctcgg atttactgcc tgaattgagt gcttcggcat atgcgtcgtt ggcagattgc   2400

tgacctcctc tagctgatct gccatcgatt tggaaaactc caaaatcaat gaagtctccg   2460

tctttctcca cgtaggtctt gacatctgtt gagctcttag ctgcctgaat gttcggatgg   2520

aaatgtgctg acctgtgtgg ggataccagg tcgaagaacc gttggttctt acattggtat   2580

ttgccttcga attggataag cacatggaga tgtggttccc cattctcgtg gagttctttg   2640

caaactttga tgtatttttt atttgttggg gtttctaggt tttttaattg ggaaagtgct   2700

tcctctttag agagagaaca attgggatat gttaggaaat aatttttggc atatatttta   2760

aataaacgag gcat                                                     2774
```

<210> SEQ ID NO 2
<211> LENGTH: 2774
<212> TYPE: DNA
<213> ORGANISM: tomato yellow leaf curl virus

<400> SEQUENCE: 2

```
gttgaaatga atcggtgtcc ctcaaagctc tatggcaacc ggtgtatcgg tgtcttattt     60
```

-continued atacctggac accgaatggc tatttggtaa tttcatgaat gttcattata attcaaaatt 120
caaaaatcaa atcattaaag cggccatccg tataatatta ccggatggcc gcgccttttc 180
cttttatgtg gtccccacga gggttacaca gacgtcactg tcaaccaatc aaattgcatc 240
ctcaaacgtt agataagtgt tcatttgtct ttatatactt ggtccccaag ttttctgtct 300
tgcaatatgt gggacccact tcttaatgag tttcctgaat ctgttcacgg atttcgttgt 360
atgttagcta ttaaatattt gcagtccgtt gaggaaactt acgagcccaa tacattgggc 420
cacgatttaa ttagggatct tatatctgtc gtaagggccc gtgactatgt cgaagcgacc 480
aggcgatata atcatttcca cgcccgtctc gaaggttcgc cgaaggctga acttcgacag 540
cccatacagc agccgtgctg ctgtccccat tgtccaaggc acaaacaagc gacgatcatg 600
gacgtacagg cccatgtacc gaaagcccag aatatacaga atgtatcgaa gccctgatgt 660
tccccgtgga tgtgaaggcc catgtaaagt ccagtcttat gagcgacggg atgatattaa 720
gcatactggt attgttcgtt gtgttagtga tgttactcgt ggatctggaa ttactcacag 780
agtgggtaag aggttctgtg ttaaatcgat atatttttta gggaaagtct ggatggatga 840
aaatatcaag aagcagaatc acactaatca ggtcatgttc ttcttagtcc gtgatagaag 900
gccctttgga agcagcccaa tggattttgg acaggttttt aatatgttcg ataatgagcc 960
cagtaccgca accgtgaata atgatttgcg ggataggttt caagtgatga ggaaatttca 1020
tgctacagtt attggtggac cctctggaat caaggaacag gcattagtta agagattttt 1080
taaaattaac agtcatgtaa cttataatca tcaggaggca gccaagtacg agaaccatac 1140
tgaaaacgcc ttgttattgt atatgtcatg tacgcatgcc tctaatccag tgtatgcaac 1200
tatgaaaata cgcatctatt tctatgattc aatatcaaat taataaaatt tatattttat 1260
atcatgagtt tctgttacat ttattgtgtt ttcaagtaca tcatacaata catgatcaac 1320
tgatctgatt acattgttaa tggaaattac accaagacta tctaaatact taagaacttc 1380
atatctaaat actcttaaga aatgaccagt ctgaggctgt aatgtcgtcc aaattcggaa 1440
gttgagaaaa catttgtgaa tccccatgac cttcctgatg ttgtggttga atcttatctg 1500
aatggaaatg atgtcgtggt tcattagaaa tggcctctgg ctgtgttctg ttatcttgaa 1560
atagagggga ttgtttatct cccagataaa aacgccattc tctgcctgag gagcagtgat 1620
gagttcccct gtgcgtgaat ccatgattat tgcagttgag gtggaggtag tatgagcagc 1680
cacagtctag gtctacacgc ttacgcctta ttggtttctt cttggctatc ttgtgttgga 1740
ccttgattga tacttgcgaa cagtggctcg tagagggtga cgaaggttgc attcttgaga 1800
gtccaatttt tcaaggatat gtttttttct tcgtctagat attccctata tgaggaggta 1860
ggtcctggat tgcagaggaa gatagtggga attccccctt taatttgaat gggcttcccg 1920
tactttgtgt tgctttgcca gtccctttgg gcccccatga attctttgaa gtgctttaaa 1980
taatgcggat ctacgtcatc aatgacgttg taccacgcat cattactgta tacctttggg 2040
cttaggtcta gatgtccaca taaataatta tgtgggccta gagacctggc ccacattgtt 2100
ttccctgttc tgctatcacc ctcaatgaca atacttatgg gtctccatgg ccgcgcagcg 2160
gaagacacga cgttctcggc gacccactct tcaagttcat ctggaacttg attaaaagaa 2220
gaagaaagaa atggagaaac ataaacttct aaaggaggac taaaaatcct atctaaattt 2280
gaacttaaat tatgaaattg taaaatatag tcctttgggg ccttctcttt taatatattg 2340
agggcctcgg atttactgcc tgaattgagt gcttcggcat atgcgtcgtt ggcagattgc 2400

-continued

```
tgacctcctc tagctgatct gccatcgatt tggaaaactc caaaatcaat gaagtctccg   2460

tctttctcca cgtaggtctt gacatctgtt gagctcttag ctgcctgaat gttcggatgg   2520

aaatgtgctg acctgtttgg ggataccagg tcgaagaacc gttggttctt acattggtat   2580

ttgccttcga attggataag cacatggaga tgtggttccc cattctcgtg gagttctttg   2640

caaactttga tgtatttttt atttgttggg gtttctaggt tttttaattg ggaaagtgct   2700

tcctctttag agagagaaca tttgggatat gttaggaaat aatttttggc atatatatta   2760

aataaacgag gcat                                                      2774
```

<210> SEQ ID NO 3
<211> LENGTH: 2774
<212> TYPE: DNA
<213> ORGANISM: tomato yellow leaf curl virus

<400> SEQUENCE: 3

```
gttgaaatga atcggtgtcc ctcaaagctc tatggcaacc ggtgtatcgg tgtcttattt     60

atacctggac accgaatggc tatttggtaa tttcatgaat gttcattata attcaaaatt    120

caaaaatcaa atcattaaag cggccatccg tataatatta ccggatggcc gcgccttttc    180

cttttatgtg gtccccacga gggttacaca gacgtcactg tcaaccaatc aaattgcatc    240

ctcaaacgtt agataagtgt tcatttgtct ttatatactt ggtccccaag ttttctgtct    300

tgcaatatgt gggacccact tcttaatgag tttcctgaat ctgttcacgg atttcgttgt    360

atgttagcta ttaaatattt gcagtccgtt gaggaaactt acgagcccaa tacattgggc    420

cacgatttaa ttagggatct tatatctgtc gtaagggccc gtgactatgt cgaagcgacc    480

aggcgatata atcatttcca cgcccgtctc gaaggttcgc cgaaggctga acttcgacag    540

cccatacagc agccgtgctg ctgtccccat tgtccaaggc acaaacaagc gacgatcatg    600

gacgtacagg cccatgtacc gaaagcccag aatatacaga atgtatcgaa gccctgatgt    660

tccccgtgga tgtgaaggcc catgtaaagt ccagtcttat gagcaacggg atgatattaa    720

gcatactggt attgttcgtt gtgttagtga tgttactcgt ggatctggaa ttactcacag    780

agtgggtaag aggttctgtg ttaaatcgat atatttttta gggaaagtct ggatggatga    840

aaatatcaag aagcagaatc acactaatca ggtcatgttc ttcttagtcc gtgatagaag    900

gccctatgga agcagcccaa tggattttgg acaggttttt aatatgttcg ataatgagcc    960

cagtaccgca accgtgaaga atgatttgcg ggataggttt caagtgatga ggaaatttca   1020

tgctacagtt attggtggac cctctggaat caaggaacag gcattagtta agagattttt   1080

taaaattaac agtcatgtaa cttataatca tcaggaggca gccaagtacg agaaccatac   1140

tgaaaacgcc ttgttattgt atatgtcatg tacgcatgcc tctaatccag tgtatgcaac   1200

tatgaaaata cgcatctatt tctatgattc aatatcaaat taataaaatt tatattttat   1260

atcatgagtt tctgttacat ttattgtgtt ttcaagtaca tcatacaata catgatcaac   1320

tgatctgatt acattgttaa tggaaattac accaagacta tctaaatact taagaacttc   1380

atatctaaat actcttaaga aatgaccagt ctgaggctgt aatgtcgtcc aaattcggaa   1440

gttgagaaaa catttgtgaa tccccatgac cttcctgatg ttgtggttga atcttatctg   1500

aatggaaatg atgtcgtggt tcattagaaa tggcctctgg ctgtgttctg ttatcttgaa   1560

atagagggga ttgtttatct cccagataaa aacgccattc tctgcctgag gagcagtgat   1620

gagttcccct gtgcgtgaat ccatgattat tgcagttgag gtggaggtag tatgagcagc   1680

cacagtctag gtctacacgc ttacgcctta ttggtttctt cttggctatc ttgtgttgga   1740
```

```
ccttgattga tacttgcgaa cagtggctcg tagagggtga cgaaggttgc attcttgaga   1800
gtccaatttt tcaaggatat gtttttttct tcgtctagat attccctata tgaggaggta   1860
ggtcctggat tgcagaggaa gatagtggga attccccctt taatttgaat gggcttcccg   1920
tactttgtgt tgctttgcca gtccctttgg gcccccatga attctttgaa gtgctttaaa   1980
taatgcggat ctacgtcatc aatgacgttg taccacgcat cattactgta tacctttggg   2040
cttaggtcta gatgtccaca taaataatta tgtgggccta gagacctggc ccacattgtt   2100
ttccctgttc tgctatcacc ctcaatgaca atacttatgg gtctccatgg ccgcgcagcg   2160
gaagacacga cgttctcggc gacccactct tcaagttcat ctggaacttg attaaaagaa   2220
gaagaaagaa atggagaaac ataaacttct aaaggaggac taaaaatcct atctaaattt   2280
gaacttaaat tatgaaattg taaaatatag tcctttgggg ccttctcttt taatatattg   2340
agggcctcgg atttactgcc tgaattgagt gcttcggcat atgcgtcgtt ggcagattgc   2400
tgacctcctc tagctgatct gccatcgatt tggaaaactc caaaatcaat gaagtctccg   2460
tctttctcca cgtaggtctt gacatctgtt gagctcttag ctgcctgaat gttcggatgg   2520
aaatgtgctg acctgtttgg ggataccagg tcgaagaacc gttggttctt acattggtat   2580
ttgccttcga attggataag cacatggaga tgtggttccc cattctcgtg gagttctttg   2640
caaactttga tgtatttttt atttgttggg gtttctaggt tttttaattg ggaaagtgct   2700
tcctctttag agagagaaca tttgggatat gttaggaaat aatttttggc atatatatta   2760
aataaacgag gcat                                                     2774
```

<210> SEQ ID NO 4
<211> LENGTH: 777
<212> TYPE: DNA
<213> ORGANISM: tomato yellow leaf curl virus

<400> SEQUENCE: 4

```
atgtcgaagc gaccaggcga tataatcatt tccacgcccg tctcgaaggt tcgccgaagg     60
ctgaacttcg acagcccata cagcagccgt gctgctgtcc ccattgtcca aggcacaaac    120
aagcgacgat catggacgta caggcccatg taccgaaagc ccagaatata cagaatgtat    180
cgaagccctg atgttccccg tggatgtgaa ggcccatgta aagtccagtc ttatgagcga    240
cgggatgata ttaagcatac tggtattgtt cgttgtgtta gtgatgttac tcgtggatct    300
ggaattactc acagagtggg taagaggttc tgtgttaaat cgatatattt tttagggaaa    360
gtctggatgg atgaaaatat caagaagcag aatcatacta atcaggtcat gttcttctta    420
gtccgtgata gaaggccctt tggaagcagc ccaatggatt ttggacaggt tttaatatg     480
ttcgataatg agcccagtac cgcaaccgtg aataatgatt tgcgggatag gtttcaagtg    540
atgaggaaat ttcatgctac agttattggt ggaccctctg gaatgaagga acaggcatta    600
gttaagagat tttttaaaat taacagtcat gtaacttata atcatcagga ggcagccaag    660
tacgagaacc atactgaaaa cgccttgtta ttgtatatgg catgtacgca tgcctctaat    720
ccagtgtatg caactatgaa aatacgcatc tatttctatg attcaatatc aaattaa       777
```

<210> SEQ ID NO 5
<211> LENGTH: 777
<212> TYPE: DNA
<213> ORGANISM: tomato yellow leaf curl virus

<400> SEQUENCE: 5

-continued

```
atgtcgaagc gaccaggcga tataatcatt tccacgcccg tctcgaaggt tcgccgaagg     60

ctgaacttcg acagcccata cagcagccgt gctgctgtcc ccattgtcca aggcacaaac    120

aagcgacgat catggacgta caggcccatg taccgaaagc ccagaatata cagaatgtat    180

cgaagccctg atgttccccg tggatgtgaa ggcccatgta aagtccagtc ttatgagcga    240

cgggatgata ttaagcatac tggtattgtt cgttgtgtta gtgatgttac tcgtggatct    300

ggaattactc acagagtggg taagaggttc tgtgttaaat cgatatattt tttagggaaa    360

gtctggatgg atgaaaatat caagaagcag aatcacacta atcaggtcat gttcttctta    420

gtccgtgata gaaggccctt tggaagcagc ccaatggatt ttggacaggt ttttaatatg    480

ttcgataatg agcccagtac cgcaaccgtg aataatgatt tgcgggatag gtttcaagtg    540

atgaggaaat ttcatgctac agttattggt ggaccctctg gaatcaagga acaggcatta    600

gttaagagat tttttaaaat taacagtcat gtaacttata atcatcagga ggcagccaag    660

tacgagaacc atactgaaaa cgccttgtta ttgtatatgt catgtacgca tgcctctaat    720

ccagtgtatg caactatgaa aatacgcatc tatttctatg attcaatatc aaattaa       777
```

<210> SEQ ID NO 6
<211> LENGTH: 777
<212> TYPE: DNA
<213> ORGANISM: tomato yellow leaf curl virus

<400> SEQUENCE: 6

```
atgtcgaagc gaccaggcga tataatcatt tccacgcccg tctcgaaggt tcgccgaagg     60

ctgaacttcg acagcccata cagcagccgt gctgctgtcc ccattgtcca aggcacaaac    120

aagcgacgat catggacgta caggcccatg taccgaaagc ccagaatata cagaatgtat    180

cgaagccctg atgttccccg tggatgtgaa ggcccatgta aagtccagtc ttatgagcaa    240

cgggatgata ttaagcatac tggtattgtt cgttgtgtta gtgatgttac tcgtggatct    300

ggaattactc acagagtggg taagaggttc tgtgttaaat cgatatattt tttagggaaa    360

gtctggatgg atgaaaatat caagaagcag aatcacacta atcaggtcat gttcttctta    420

gtccgtgata gaaggcccta tggaagcagc ccaatggatt ttggacaggt ttttaatatg    480

ttcgataatg agcccagtac cgcaaccgtg aagaatgatt tgcgggatag gtttcaagtg    540

atgaggaaat ttcatgctac agttattggt ggaccctctg gaatcaagga acaggcatta    600

gttaagagat tttttaaaat taacagtcat gtaacttata atcatcagga ggcagccaag    660

tacgagaacc atactgaaaa cgccttgtta ttgtatatgt catgtacgca tgcctctaat    720

ccagtgtatg caactatgaa aatacgcatc tatttctatg attcaatatc aaattaa       777
```

<210> SEQ ID NO 7
<211> LENGTH: 258
<212> TYPE: PRT
<213> ORGANISM: tomato yellow leaf curl virus

<400> SEQUENCE: 7

```
Met Ser Lys Arg Pro Gly Asp Ile Ile Ile Ser Thr Pro Val Ser Lys
1               5                   10                  15

Val Arg Arg Arg Leu Asn Phe Asp Ser Pro Tyr Ser Ser Arg Ala Ala
            20                  25                  30

Val Pro Ile Val Gln Gly Thr Asn Lys Arg Arg Ser Trp Thr Tyr Arg
        35                  40                  45

Pro Met Tyr Arg Lys Pro Arg Ile Tyr Arg Met Tyr Arg Ser Pro Asp
    50                  55                  60
```

Val Pro Arg Gly Cys Glu Gly Pro Cys Lys Val Gln Ser Tyr Glu Arg
65 70 75 80

Arg Asp Asp Ile Lys His Thr Gly Ile Val Arg Cys Val Ser Asp Val
85 90 95

Thr Arg Gly Ser Gly Ile Thr His Arg Val Gly Lys Arg Phe Cys Val
100 105 110

Lys Ser Ile Tyr Phe Leu Gly Lys Val Trp Met Asp Glu Asn Ile Lys
115 120 125

Lys Gln Asn His Thr Asn Gln Val Met Phe Phe Leu Val Arg Asp Arg
130 135 140

Arg Pro Phe Gly Ser Ser Pro Met Asp Phe Gly Gln Val Phe Asn Met
145 150 155 160

Phe Asp Asn Glu Pro Ser Thr Ala Thr Val Asn Asn Asp Leu Arg Asp
165 170 175

Arg Phe Gln Val Met Arg Lys Phe His Ala Thr Val Ile Gly Gly Pro
180 185 190

Ser Gly Met Lys Glu Gln Ala Leu Val Lys Arg Phe Phe Lys Ile Asn
195 200 205

Ser His Val Thr Tyr Asn His Gln Glu Ala Ala Lys Tyr Glu Asn His
210 215 220

Thr Glu Asn Ala Leu Leu Leu Tyr Met Ala Cys Thr His Ala Ser Asn
225 230 235 240

Pro Val Tyr Ala Thr Met Lys Ile Arg Ile Tyr Phe Tyr Asp Ser Ile
245 250 255

Ser Asn

<210> SEQ ID NO 8
<211> LENGTH: 258
<212> TYPE: PRT
<213> ORGANISM: tomato yellow leaf curl virus

<400> SEQUENCE: 8

Met Ser Lys Arg Pro Gly Asp Ile Ile Ile Ser Thr Pro Val Ser Lys
1 5 10 15

Val Arg Arg Arg Leu Asn Phe Asp Ser Pro Tyr Ser Ser Arg Ala Ala
20 25 30

Val Pro Ile Val Gln Gly Thr Asn Lys Arg Arg Ser Trp Thr Tyr Arg
35 40 45

Pro Met Tyr Arg Lys Pro Arg Ile Tyr Arg Met Tyr Arg Ser Pro Asp
50 55 60

Val Pro Arg Gly Cys Glu Gly Pro Cys Lys Val Gln Ser Tyr Glu Arg
65 70 75 80

Arg Asp Asp Ile Lys His Thr Gly Ile Val Arg Cys Val Ser Asp Val
85 90 95

Thr Arg Gly Ser Gly Ile Thr His Arg Val Gly Lys Arg Phe Cys Val
100 105 110

Lys Ser Ile Tyr Phe Leu Gly Lys Val Trp Met Asp Glu Asn Ile Lys
115 120 125

Lys Gln Asn His Thr Asn Gln Val Met Phe Phe Leu Val Arg Asp Arg
130 135 140

Arg Pro Phe Gly Ser Ser Pro Met Asp Phe Gly Gln Val Phe Asn Met
145 150 155 160

Phe Asp Asn Glu Pro Ser Thr Ala Thr Val Asn Asn Asp Leu Arg Asp
165 170 175

```
Arg Phe Gln Val Met Arg Lys Phe His Ala Thr Val Ile Gly Gly Pro
            180                 185                 190

Ser Gly Ile Lys Glu Gln Ala Leu Val Lys Arg Phe Phe Lys Ile Asn
        195                 200                 205

Ser His Val Thr Tyr Asn His Gln Glu Ala Ala Lys Tyr Glu Asn His
    210                 215                 220

Thr Glu Asn Ala Leu Leu Leu Tyr Met Ser Cys Thr His Ala Ser Asn
225                 230                 235                 240

Pro Val Tyr Ala Thr Met Lys Ile Arg Ile Tyr Phe Tyr Asp Ser Ile
                245                 250                 255

Ser Asn


<210> SEQ ID NO 9
<211> LENGTH: 258
<212> TYPE: PRT
<213> ORGANISM: tomato yellow leaf curl virus

<400> SEQUENCE: 9

Met Ser Lys Arg Pro Gly Asp Ile Ile Ile Ser Thr Pro Val Ser Lys
1               5                   10                  15

Val Arg Arg Arg Leu Asn Phe Asp Ser Pro Tyr Ser Ser Arg Ala Ala
            20                  25                  30

Val Pro Ile Val Gln Gly Thr Asn Lys Arg Arg Ser Trp Thr Tyr Arg
        35                  40                  45

Pro Met Tyr Arg Lys Pro Arg Ile Tyr Arg Met Tyr Arg Ser Pro Asp
    50                  55                  60

Val Pro Arg Gly Cys Glu Gly Pro Cys Lys Val Gln Ser Tyr Glu Gln
65                  70                  75                  80

Arg Asp Asp Ile Lys His Thr Gly Ile Val Arg Cys Val Ser Asp Val
                85                  90                  95

Thr Arg Gly Ser Gly Ile Thr His Arg Val Gly Lys Arg Phe Cys Val
            100                 105                 110

Lys Ser Ile Tyr Phe Leu Gly Lys Val Trp Met Asp Glu Asn Ile Lys
        115                 120                 125

Lys Gln Asn His Thr Asn Gln Val Met Phe Phe Leu Val Arg Asp Arg
    130                 135                 140

Arg Pro Tyr Gly Ser Ser Pro Met Asp Phe Gly Gln Val Phe Asn Met
145                 150                 155                 160

Phe Asp Asn Glu Pro Ser Thr Ala Thr Val Lys Asn Asp Leu Arg Asp
                165                 170                 175

Arg Phe Gln Val Met Arg Lys Phe His Ala Thr Val Ile Gly Gly Pro
            180                 185                 190

Ser Gly Ile Lys Glu Gln Ala Leu Val Lys Arg Phe Phe Lys Ile Asn
        195                 200                 205

Ser His Val Thr Tyr Asn His Gln Glu Ala Ala Lys Tyr Glu Asn His
    210                 215                 220

Thr Glu Asn Ala Leu Leu Leu Tyr Met Ser Cys Thr His Ala Ser Asn
225                 230                 235                 240

Pro Val Tyr Ala Thr Met Lys Ile Arg Ile Tyr Phe Tyr Asp Ser Ile
                245                 250                 255

Ser Asn


<210> SEQ ID NO 10
<211> LENGTH: 20
```

-continued

<212> TYPE: DNA
<213> ORGANISM: Artificial
<220> FEATURE:
<223> OTHER INFORMATION: primer

<400> SEQUENCE: 10
ccctctggaa tgaaggaaca 20

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
ttgaaaaatt ggrctctcaa 20

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
tataagctta ggcatgttga aatgaatcgg 30

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13
gattagaggc atgcgtacat g 21

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
gtacgcatgc ctctaatcca g 21

<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15
atggatccga aactcattaa gaagtgggtc 30

<210> SEQ ID NO 16
<211> LENGTH: 29
<212> TYPE: DNA
<213> ORGANISM: Artificial
<220> FEATURE:
<223> OTHER INFORMATION: primer

<400> SEQUENCE: 16
ksgggtcgac gtcatcaatg acgttrtac 29

<210> SEQ ID NO 17
<211> LENGTH: 31
<212> TYPE: DNA
<213> ORGANISM: Artificial
<220> FEATURE:
<223> OTHER INFORMATION: primer

<400> SEQUENCE: 17
gatttctgca gttdatrtty tcrtccatcc a 31

<210> SEQ ID NO 18
<211> LENGTH: 26
<212> TYPE: DNA
<213> ORGANISM: Artificial
<220> FEATURE:
<223> OTHER INFORMATION: primer

<400> SEQUENCE: 18
agtattgtca ttgagggtga tagcag 26

<210> SEQ ID NO 19
<211> LENGTH: 27
<212> TYPE: DNA
<213> ORGANISM: Artificial
<220> FEATURE:
<223> OTHER INFORMATION: primer

<400> SEQUENCE: 19
gcccatgtaa agtccagtct tatgagc 27

<210> SEQ ID NO 20
<211> LENGTH: 10
<212> TYPE: PRT
<213> ORGANISM: tomato leaf yellow curl virus
<220> FEATURE:
<221> NAME/KEY: NON_CONS
<222> LOCATION: (1)..(10)

<400> SEQUENCE: 20

Val Arg Phe Asn Met Ala Pro Gln Ser His
1 5 10

<210> SEQ ID NO 21
<211> LENGTH: 10
<212> TYPE: PRT
<213> ORGANISM: tomato yellow leaf curl virus
<220> FEATURE:
<221> NAME/KEY: NON_CONS
<222> LOCATION: (1)..(10)

<400> SEQUENCE: 21

Leu Gln Tyr Lys Ile Ser Pro Leu Ser Gln
1 5 10

<210> SEQ ID NO 22
<211> LENGTH: 10
<212> TYPE: PRT
<213> ORGANISM: tomato yellow leaf curl virus
<220> FEATURE:
<221> NAME/KEY: NON_CONS
<222> LOCATION: (1)..(10)

<400> SEQUENCE: 22

Leu Gln Tyr Lys Ile Ser Pro Leu Ser Gln
1 5 10

-continued

<210> SEQ ID NO 23
<211> LENGTH: 10
<212> TYPE: PRT
<213> ORGANISM: tomato yellow leaf curl virus
<220> FEATURE:
<221> NAME/KEY: NON_CONS
<222> LOCATION: (1)..(10)

<400> SEQUENCE: 23

```
Leu Gln Tyr Lys Met Ala Pro Leu Ser Gln
1               5                   10
```

<210> SEQ ID NO 24
<211> LENGTH: 10
<212> TYPE: PRT
<213> ORGANISM: tomato yellow leaf curl virus
<220> FEATURE:
<221> NAME/KEY: NON_CONS
<222> LOCATION: (1)..(10)

<400> SEQUENCE: 24

```
Leu Gln Tyr Lys Met Ala Pro Leu Ser Gln
1               5                   10
```

<210> SEQ ID NO 25
<211> LENGTH: 10
<212> TYPE: PRT
<213> ORGANISM: tomato yellow leaf curl virus
<220> FEATURE:
<221> NAME/KEY: NON_CONS
<222> LOCATION: (1)..(10)

<400> SEQUENCE: 25

```
Leu Gln Tyr Lys Met Ala Arg Leu Pro Gln
1               5                   10
```

<210> SEQ ID NO 26
<211> LENGTH: 10
<212> TYPE: PRT
<213> ORGANISM: tomato yellow leaf curl virus
<220> FEATURE:
<221> NAME/KEY: NON_CONS
<222> LOCATION: (1)..(10)

<400> SEQUENCE: 26

```
Lys Asn Gly Phe His Asn Asp Met Val Ser
1               5                   10
```

<210> SEQ ID NO 27
<211> LENGTH: 10
<212> TYPE: PRT
<213> ORGANISM: tomato yellow leaf curl virus
<220> FEATURE:
<221> NAME/KEY: NON_CONS
<222> LOCATION: (1)..(10)

<400> SEQUENCE: 27

```
Asn Lys Gly Phe Asn Ser Asp Ile Ile Ala
1               5                   10
```

<210> SEQ ID NO 28
<211> LENGTH: 10
<212> TYPE: PRT
<213> ORGANISM: tomato yellow leaf curl virus
<220> FEATURE:
<221> NAME/KEY: NON_CONS
<222> LOCATION: (1)..(10)

-continued

```
<400> SEQUENCE: 28

Asn Lys Glu Phe Asn Ser Asp Ile Ile Ala
1               5                   10


<210> SEQ ID NO 29
<211> LENGTH: 10
<212> TYPE: PRT
<213> ORGANISM: tomato yellow leaf curl virus
<220> FEATURE:
<221> NAME/KEY: NON_CONS
<222> LOCATION: (1)..(10)

<400> SEQUENCE: 29

Asn Asn Gly Phe Asn Ser Gly Ile Ile Ala
1               5                   10


<210> SEQ ID NO 30
<211> LENGTH: 10
<212> TYPE: PRT
<213> ORGANISM: tomato yellow leaf curl virus
<220> FEATURE:
<221> NAME/KEY: NON_CONS
<222> LOCATION: (1)..(10)

<400> SEQUENCE: 30

Asn Asn Gly Phe Asn Ser Asp Ile Ile Ala
1               5                   10


<210> SEQ ID NO 31
<211> LENGTH: 10
<212> TYPE: PRT
<213> ORGANISM: tomato yellow leaf curl virus
<220> FEATURE:
<221> NAME/KEY: NON_CONS
<222> LOCATION: (1)..(10)

<400> SEQUENCE: 31

Asn Asn Gly Ser Asn Ser Asp Ile Ile Ala
1               5                   10
```